US006861022B2

(12) United States Patent
Robinson et al.

(10) Patent No.: US 6,861,022 B2
(45) Date of Patent: Mar. 1, 2005

(54) PROCESS AND PRESS FOR THE PRODUCTION OF TABLETS

(75) Inventors: Paul William Robinson, Swanland (GB); Manuela Bosco, Lanzago di Silea (IT); Peer Karkutsch, Darnstadt (DE)

(73) Assignee: Reckitt Benckiser N.V., Hoofddorp (NL)

( * ) Notice: Subject to any disclaimer, the term of this patent is extended or adjusted under 35 U.S.C. 154(b) by 143 days.

(21) Appl. No.: 10/276,041
(22) PCT Filed: May 9, 2001
(86) PCT No.: PCT/GB01/02026
§ 371 (c)(1),
(2), (4) Date: Mar. 28, 2003
(87) PCT Pub. No.: WO01/85437
PCT Pub. Date: Nov. 15, 2001

(65) Prior Publication Data
US 2003/0160353 A1 Aug. 28, 2003

(30) Foreign Application Priority Data
May 11, 2000 (GB) ............................................. 0011382

(51) Int. Cl.⁷ .......................... B29B 11/12; B28B 21/00
(52) U.S. Cl. ....................... 264/113; 264/119; 264/120; 425/355; 425/422
(58) Field of Search ................................ 264/113, 119, 264/120; 425/355, 422

(56) References Cited

U.S. PATENT DOCUMENTS 5,417,903 A  *  5/1995  Harrison et al. ............. 264/109
5,616,552 A  *  4/1997  Yoshihara et al. ........... 510/490

FOREIGN PATENT DOCUMENTS

| DE | 910 629 C | 5/1954 | |
|---|---|---|---|
| DE | 35 07 222 A | 8/1986 | ............ C06B/21/00 |
| GB | 1585699 | 12/1977 | ............ B30B/11/00 |
| JP | 6218586 | 8/1994 | ............ B30B/11/00 |
| JP | 8332596 | 12/1996 | ............ B30B/11/08 |
| WO | WO 00/10800 | 3/2000 | ............ B30B/11/08 |

OTHER PUBLICATIONS

PCT International Search Report for PCT/GB01/02026.
GB Search Report Search Report for GB 0011382.9 dated Nov. 14, 2000.

* cited by examiner

Primary Examiner—Stephen J. Lechert, Jr.
(74) Attorney, Agent, or Firm—Norris McLaughlin & Marcus PA

(57) ABSTRACT

A process for the production of tablets with a cavity using a press, equipped with upper and lower punches, the lower punch comprising a ring portion being able to reciprocate, characterized in that a central member is provided within the ring portion of the lower punch, this central member being fixed in a pre-determined position beneath the upper part of the die during the process and that, at some stage before the first compression step, the ring portion of the lower punch is adjusted at a position beneath the level of the upper end of the central member.

11 Claims, 3 Drawing Sheets

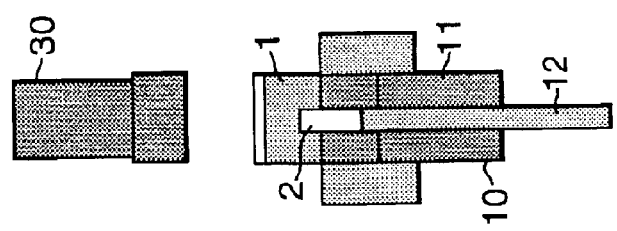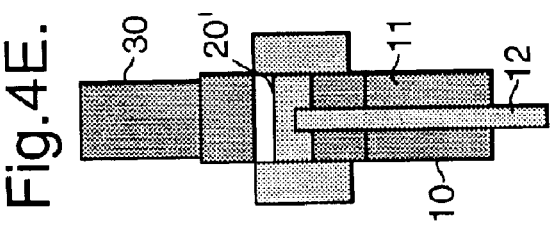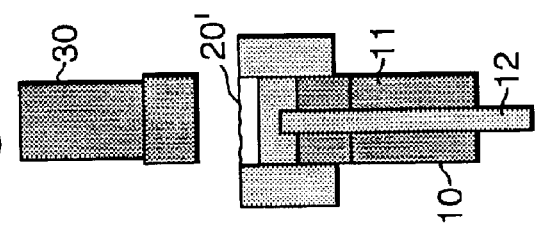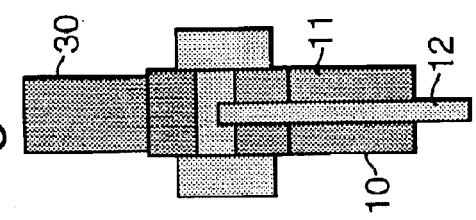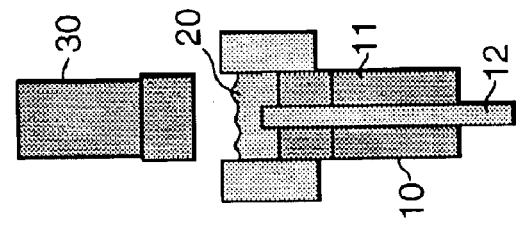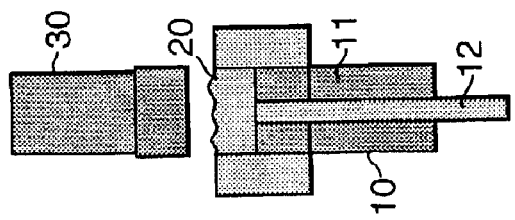

PROCESS AND PRESS FOR THE PRODUCTION OF TABLETS

The invention is related to a process and press for the production of tablets with a cavity.

Tablets with cavities to receive an additional ingredient or mix of ingredients are known from prior art. WO99/6157, for example, describes such type of tablets, manufactured from a particulate material, for laundry washing or automatic dishwashing purposes.

This type of tablet is usually manufactured by providing a protrusion in the upper punch of the press (preferably rotary press) which creates the cavity during compression. As a consequence of the creation of such cavity, the region beneath and adjacent to the sides of the cavity is compressed to a much higher extent than the rest of the tablet creating an uneven distribution of densities within the tablet.

This uneven distribution entails the consequence that different portions of the tablet show different disintegration and solubilization profiles. Also when reducing the overall pressure of the upper punch in order not to inappropriately increase the density of the tablet in specific regions, the lighter pressure might easily result in an insufficient compression of the shoulders of the tablet which would then become too friable for practical purposes.

To some extent a compensation of the uneven solubilization behaviour could be achieved by an uneven distribution of binders and disintegrating agents within the tablet, which, however, would substantially add to the complexity and costs of the tablet.

U.S. Pat. No. 3,840,361 discloses a method of making composite tablets having an annular first portion and centrally disposed second portion, using a lower punch consisting of a ring portion and a central portion which are both displaced relative to each other and relative to the upper punch during the process. No manufacture of tablets with a cavity is disclosed.

A similar process is described in WO 00/10800, again with a lower punch consisting of a ring portion and a central portion which can be displaced independently from and parallel in relation to each other. In one embodiment, the manufacture of a two-layer tablet with a cavity in one of those layers is disclosed. The process, however, requires several steps of moves of both portions of the lower punch.

Therefore, there is a need in the art of finding a more effective manufacturing process for pressing tablets with cavities avoiding the above mentioned disadvantages.

This need is met by a process for the production of tablets with a cavity using a press, equipped with upper and lower punches, the lower punch comprising of a ring portion being able to reciprocate wherein a central member is provided within the ring portion of the lower punch, this central member being fixed in a pre-determined position beneath the upper part of the die during the process and that, at some stage before the first compression step, the ring portion of the lower punch is adjusted at a position beneath the level of the upper end of the central member.

In one embodiment, the ring portion of the lower punch is lowered to a position beneath the level of the upper end of the central member; a pre-mix is filled into the die; the pre-mix is pressed between the upper punch and the ring portion of the lower punch, the upper surface of the ring portion of the lower punch staying beneath the upper end of the central member during this compression step; and, after raising the upper punch again, the tablet is ejected by raising the ring portion of the lower punch.

In a further embodiment, after filling the pre-mix into the die and optionally pre-compressing the pre-mix, another pre-mix for a second layer is filled into the die.

In another embodiment, the ring portion of the lower punch is lowered to a position beneath the upper level of the die, but not beneath the upper end of the central member; that a pre-mix is filled into the die; that the ring portion of the lower punch is adjusted at a position beneath the upper end of the central member; that the pre-mix is compressed; and that, after raising the upper punch again, the tablet is ejected by raising the ring portion of the lower punch.

Also, after filling the pre-mix into the die and optionally pre-compressing the pre-mix, another pre-mix for a second layer can be filled into the die.

Additionally the invention is related to a press for the production of tablets with a cavity, the press being equipped with upper and lower punches, the lower punch comprising a ring portion being able to reciprocate, wherein the press is provided with a central member within the ring portion of the lower punch, this central member being fixed in a pre-determined position beneath the upper level of the die during the production process.

In one alternative, the central member is a movable central portion of the lower punch.

In another alternative, the central member is an integral central part of the die protruding from the bottom thereof.

Preferably, the central member has a circular, elliptical or rectangular horizontal cross-section.

The new press may comprise either a composite lower punch with a central portion and a movable ring portion or, within a lower punch in the form of a ring, a central member protruding as an integral part of the die from the bottom thereof. In the first alternative, the position of the central portion of the lower punch may be varied, but will not be changed during the compression process, i.e. is fixed during the production in a pre-determined position.

In a first embodiment of the invention, which is preferred for the production of mono-layer tablets, the central member is in a position between the upper end of the die and the upper surface of the ring portion of the lower punch. This reserves a central space in the die that will not be filled when the die is filled with the material to be compressed, therefore pre-creating a cavity in the uncompressed material. During the compression step either only the upper punch or, preferably, both the upper punch and the ring portion of the lower punch are moved to effect compression of the material held in the die. This creates a final compressed tablet by reducing the space occupied by the material to be compressed and, in the latter case, also the space of the pre-created cavity.

A second embodiment of the invention, although useful for the production of mono-layer tablets, is preferred for the production of multi-layer tablets and thus described in more detail for this latter type of tablets. In the initial step of this embodiment of the inventive process, the ring portion of the lower punch is at the same level as the central member (or may even be in a higher position). Then, a first pre-mix is filled into the die to form a first layer. After filling, the ring portion of the lower punch is lowered beneath the level of the central member. Gravity pulls the filled powder down and the fixed central member pre-creates a cavity in the uncompressed material. Then pre-compression may take place or not. Pre-compression may be recommendable to level the height of the powder, but is not mandatory. Subsequently, a second pre-mix is filled into the vacant space created in the die, and then the tablet is finally pressed. The latter process steps may, of course, be also repeated to form multi-layer tablets with even more than two layers, if desired.

First results clearly show that the new process conducted with the new press guarantees better physical properties of the tablets, in particular more even distribution of densities within the tablet and therefore better overall stability and more even solubilization behaviour.

The first embodiment of the invention is described in more detail by way of example of the production of mono-layer tablet.

BRIEF DESCRIPTION OF THE DRAWINGS

FIGS. 4A–F show another embodiment of a press according to the present invention and the main process steps for the production of two-layer tablets.

In FIG. 1, the density of the compressed material is higher when the shading is darker. It is obvious that beneath and to the sides of the cavity 2 the density is higher, whereas the density decreases towards the shoulders and sides of the tablet 1 resulting in the above described disadvantages.

Figure 2A:
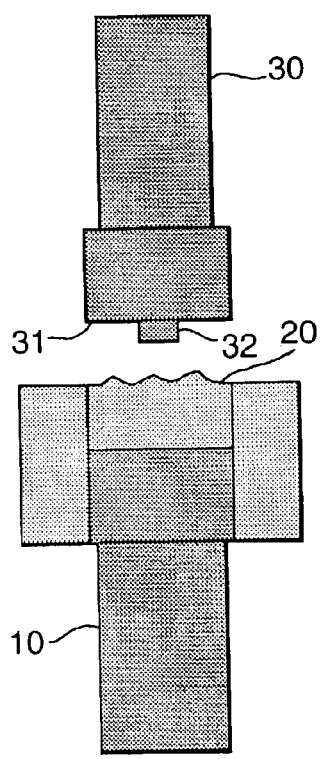
FIGS. 2A–C show a process of prior art for producing such tablet.
Figure 2B:
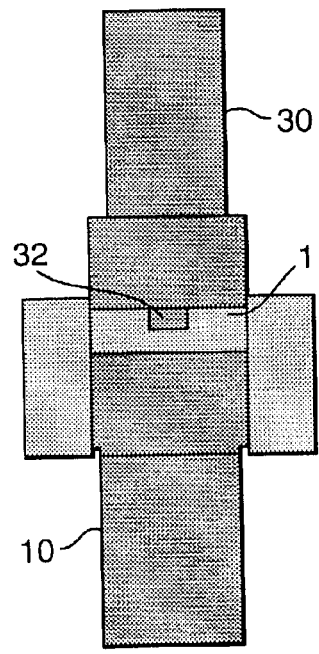
Figure 2C:
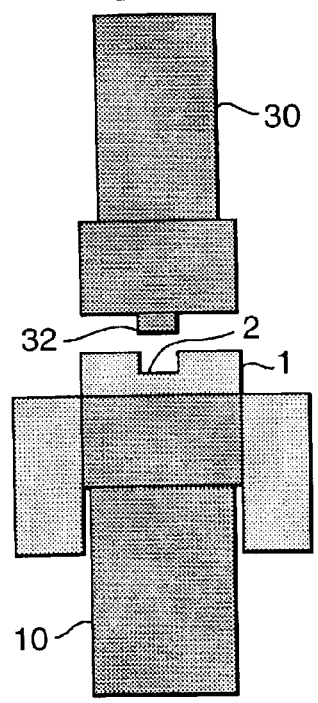

One process of prior art to produce such tablets is shown in FIGS. 2A–C.

Figure 1:
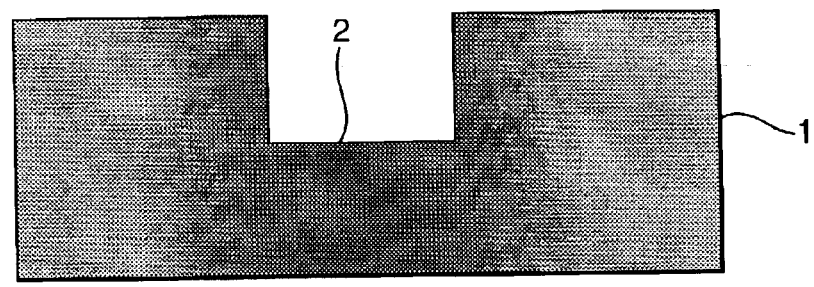
FIG. 1 shows a tablet with a cavity produced according to a prior art process the shading representing the distribution of densities.

In FIG. 2A the lower punch 10 of the press is lowered beneath the upper end of the die and the die is filled with the material 20 to be compressed. The upper punch 30, having a protrusion 32 from its bottom face 31, is lowered into the die to compress the material 20 (FIG. 2B). Then, the upper punch 30 is raised again, as well as the lower punch to eject the compressed tablet. Such tablet typically shows the distribution of densities as shown in FIG. 1 and explained herein above.

Figure 3A:
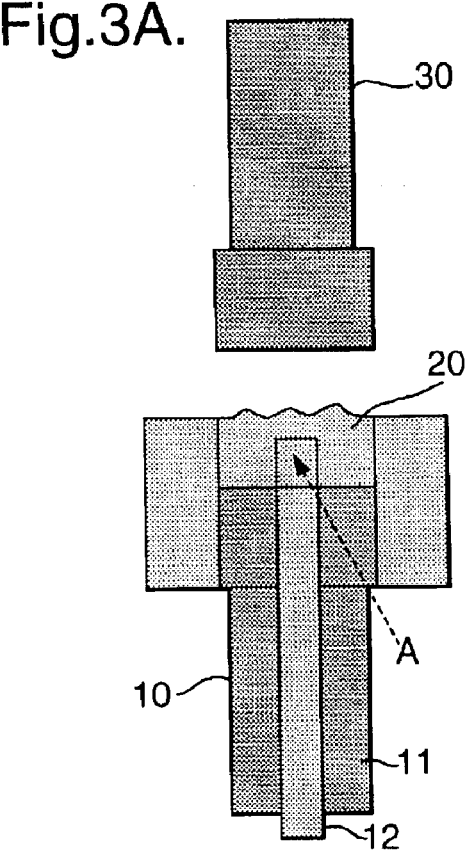
FIGS. 3A–C show one embodiment of a press according to the present invention and the main process steps for the production of mono-layer tablets.
Figure 3B:
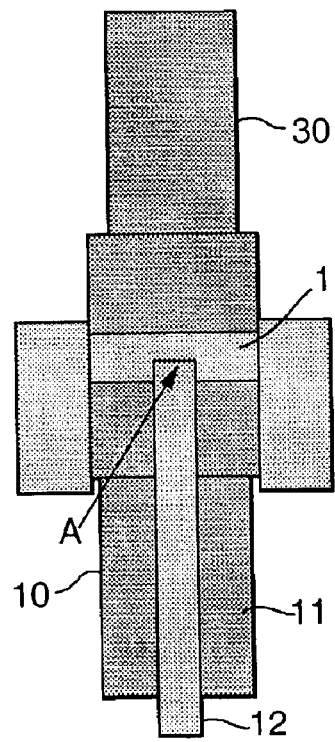
Figure 3C:
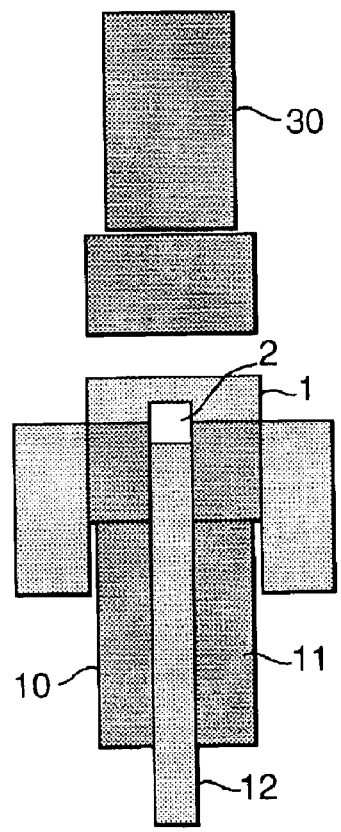

One embodiment of a press according to the present invention and process for the production of mono-layer tablets is shown in more detail in FIGS. 3A–C.

The lower punch 10 of the press consists of a ring portion 11 and a central portion 12. In an alternative, the central member 12 may be an integral part of the die protruding from the bottom thereof and the lower punch 10 may consist of the ring portion 11 only enclosing the central member 12. If the central portion 12 is part of the lower punch 10 (and not integral with the bottom of the die), it can be adjusted in height. In any case, however, the central member 12 is fixed during the compression process, i.e. held in a pre-determined position as shown in the drawings.

In the first step of the process shown in FIG. 3, the ring portion 11 of the lower punch 10 is lowered beneath the level of the upper end of the central portion 12 of the lower punch 10. When the material 20 to be compressed has been filled into the die, a cavity in the uncompressed material is pre-created as marked by arrow A.

In the second step of the compression process, simultaneously the ring portion 11 of the lower punch 10 and the upper punch 30 (which has no protrusion) are moved as shown in FIG. 3B to compress the material in the die. The second step may also be achieved by only moving, i.e. lowering, the upper punch 30, although the results would be somewhat less favourable. Although the space marked by arrow A is reduced by the rise of the ring portion 11 of the lower punch 10, it is still sufficient to create a cavity 2 in the final tablet 1. The tablet 1 is ejected by the rise of the ring portion 11 of the lower punch 10, after removal of the upper punch 30 (FIG. 3C).

Another embodiment of the press according to the present invention and a process for the production of two-layer tablets is shown in more detail in FIGS. 4A–F.

Once again, the lower punch 10 of the press consists of a ring portion 11 and a central portion 12 (or, in an alternative, a central member as an integral part of the die, as explained hereinabove).

In the first step of the process shown in FIG. 4, the ring portion 11 of the lower punch 10 is level with the central portion 12 thereof. The material 20 for the first layer is filled into the die. Then, the ring portion 11 of the lower punch 10 is lowered to pre-create a cavity in the uncompressed material and to simultaneously create more space in the die for further material 20' for the second layer.

In the next step, the upper punch 30 is lowered to compress (or pre-compress) the first layer of the tablet. Then, the material 20' for the second layer is filled into the die. The whole contents of the die is compressed to form the final tablet 1. This tablet 1 is then ejected by the rise of the ring portion 11 of the lower punch, after removal of the upper punch 30.

The features disclosed in the foregoing description, in the claims and/or drawings in the accompanying drawings may, both separately and in any combination thereof, be material for realizing the invention in diverse forms thereof.

What is claimed is:

1. A process for the production of tablets with a cavity using a press, equipped with upper and lower punches, the lower punch comprising a ring portion being able to reciprocate, characterized in that a central member is provided within the ring portion of the lower punch, this central member being fixed in a pre-determined position beneath the upper part of the die during the process and that, at some stage before the first compression step, the ring portion of the lower punch is adjusted at a position beneath the level of the upper end of the central member.

2. The process according to claim 1, characterized in that the ring portion of the lower punch is lowered to a position beneath the level of the upper end of the central member; that a pre-mix is filled into the die; that the pro-mix is pressed between the upper punch and the ring portion of the lower punch, the upper surface of the ring portion of the lower punch staying beneath the upper end of the central member during this compression step, and that, after raising the upper punch again, the tablet is ejected by raising the ring portion of the lower punch.

3. The process according to claim 2, characterized in that, after filling the pre-mix into the die and optionally pre-compressing the pre-mix, another pre-mix for a second layer is filled into the die.

4. The process according to claim 1, characterized in the ring portion of the lower punch is lowered to a position beneath the upper level of the die, but not beneath the upper end of the central member; that a pre-mix is filled into the die; that the ring portion of the lower punch is adjusted at a position beneath the upper end of the central member; that the pre-mix is compressed; and that, after raising the upper punch again, the tablet is ejected by raising the ring portion of the lower punch.

5. The process according to claim 4, characterized in that, after tilling the pre-mix into the die and optionally pre-compressing the pre-mix, another pre-mix for a second layer is filled into the die.

6. A press for the production of tablets with a cavity, the press being equipped with upper and lower punches, the lower punch comprising a ring portion being able to reciprocate, characterized in that the press is provided with a central member within the ring portion of the lower punch, this central member being fixed in a pre-determined position beneath the upper level of the die during the production process.

7. The press according to claim 6, characterized in that the central member is a movable central portion of the lower punch.

8. The press according to claim 6, characterized in that the central member is an integral central part of the die protruding from the bottom thereof.

9. The press according to claim 6 characterized in that the central member has a circular, elliptical or rectangular horizontal cross-section.

10. The press according to claim 7 characterized in that the central member has a circular, elliptical or rectangular horizontal cross-section.

11. The press according to claim 8 characterized in that the central member has a circular, elliptical or rectangular horizontal cross-section.

* * * * *